(12) United States Patent
Brengartner et al.

(10) Patent No.: US 10,078,005 B2
(45) Date of Patent: Sep. 18, 2018

(54) METHOD FOR CALIBRATION OR ADJUSTMENT OF ANY OSCILLATABLE UNIT

(71) Applicant: Endress + Hauser GmbH + Co. KG, Maulburg (DE)

(72) Inventors: Tobias Brengartner, Emmendingen (DE); Gerd Bechtel, Steinen (DE); Sascha D'Angelico, Rummingen (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 163 days.

(21) Appl. No.: 14/896,937

(22) PCT Filed: May 19, 2014

(86) PCT No.: PCT/EP2014/060190
§ 371 (c)(1),
(2) Date: Dec. 9, 2015

(87) PCT Pub. No.: WO2014/198493
PCT Pub. Date: Dec. 18, 2014

(65) Prior Publication Data
US 2016/0138964 A1    May 19, 2016

(30) Foreign Application Priority Data
Jun. 13, 2013 (DE) .......................... 10 2013 106 172

(51) Int. Cl.
*G01C 19/00* (2013.01)
*G01C 25/00* (2006.01)
(Continued)

(52) U.S. Cl.
CPC ......... *G01H 3/005* (2013.01); *G01F 23/2966* (2013.01); *G01F 25/0061* (2013.01);
(Continued)

(58) Field of Classification Search
None
See application file for complete search history.

(56) References Cited

U.S. PATENT DOCUMENTS

| | | |
|---|---|---|
| 5,687,100 A | 11/1997 | Buttler et al. |
| 6,718,270 B2 | 4/2004 | Horiuchi et al. |
| (Continued) | | |

FOREIGN PATENT DOCUMENTS

| | | |
|---|---|---|
| DE | 39703981 T2 | 5/2001 |
| EP | 2041529 B1 | 4/2009 |
| (Continued) | | |

OTHER PUBLICATIONS

English Translation of International Preliminary Report on Patentability, WIPO, Geneva, dated Dec. 23, 2015.
(Continued)

*Primary Examiner* — David M Gray
*Assistant Examiner* — Geoffrey T Evans
(74) *Attorney, Agent, or Firm* — Bacon & Thomas, PLLC

(57) ABSTRACT

A method for calibration or adjustment of any oscillatable unit with a mathematical model describing the oscillatable unit, wherein the oscillatable unit interacts with a medium located in a container, comprising the steps as follows: exciting the oscillatable unit via a real input signal to execute oscillations; the real output signal of the oscillatable unit is ascertained; the real output signal is digitized and a real output sequence is produced; the real input signal is digitized and a digital input sequence is produced; the digital input sequence is fed to a function block, which provides the mathematical model of the oscillatable unit in interaction with the medium. The mathematical model is defined by at least two sensor-specific variables; a virtual output sequence is produced via the mathematical model. The virtual output sequence is compared with the real output sequence; in the
(Continued)

case of a deviation, the sensor-specific variables of the mathematical model are adaptively changed, until the deviation between the virtual output sequence and the real output sequence of the oscillatable unit lies within a predetermined tolerance range.

9 Claims, 3 Drawing Sheets

(51) Int. Cl.
    *G01D 18/00*     (2006.01)
    *G01F 25/00*     (2006.01)
    *G06F 19/00*     (2018.01)
    *G01H 3/00*     (2006.01)
    *G01F 23/296*     (2006.01)
    *G01N 11/16*     (2006.01)
    *G01N 9/00*     (2006.01)
    *G01N 11/00*     (2006.01)

(52) U.S. Cl.
    CPC ............... *G01N 9/00* (2013.01); *G01N 11/16* (2013.01); *G01N 9/002* (2013.01); *G01N 2011/0006* (2013.01)

(56) References Cited

U.S. PATENT DOCUMENTS

| | | | |
|---|---|---|---|
| 7,043,969 B2 | 5/2006 | Matslev et al. | |
| 7,356,427 B2 | 4/2008 | Dykstra et al. | |
| 8,220,313 B2 | 7/2012 | Lopatin et al. | |
| 8,869,597 B2* | 10/2014 | Brengartner | G01F 23/2961 73/32 A |
| 2008/0055091 A1* | 3/2008 | Song | G06K 7/10237 340/572.5 |
| 2009/0228220 A1 | 9/2009 | Borgstadt | |
| 2010/0241407 A1* | 9/2010 | Hsu | G01N 11/16 703/2 |
| 2011/0001567 A1* | 1/2011 | Nicholls | H03L 1/026 331/25 |
| 2012/0101625 A1* | 4/2012 | Niemann | B22D 11/16 700/200 |
| 2012/0119758 A1* | 5/2012 | Urban | G01F 23/2965 324/617 |
| 2012/0239301 A1 | 9/2012 | Kischkat | |

FOREIGN PATENT DOCUMENTS

| | | |
|---|---|---|
| WO | 3231471 A2 | 4/2002 |
| WO | 2004036191 A1 | 4/2004 |
| WO | 2006072788 A2 | 7/2006 |
| WO | 2009118542 A1 | 10/2009 |

OTHER PUBLICATIONS

International Search Report EPO, The Netherlands, dated Oct. 30, 2014.

German Search Report, German PTO, Munich, dated Dec. 13, 2013.

* cited by examiner

METHOD FOR CALIBRATION OR ADJUSTMENT OF ANY OSCILLATABLE UNIT

TECHNICAL FIELD

The invention relates to a method for calibration or adjustment of any oscillatable unit used in process automation. The oscillatable unit interacts at least at times with a medium located in a container and is especially used for ascertaining or monitoring at least one sensor- and/or system specific parameter. In such case, process-specific parameters deliver information concerning process conditions reigning in the process, in which the oscillatable unit is arranged. Sensor-specific variables relate to influencing factors, which characterize the behavior of the oscillatable unit in the medium. These variables include especially geometric parameters and/or they concern the material properties and/or mass ratios of the oscillatable unit.

BACKGROUND DISCUSSION

The use of vibronic sensors for determining physical variables is widely distributed in automation technology—especially in process automation technology and in manufacturing automation technology. The oscillatable element of a vibronic sensor is connected by material-bonding and/or by force interlocking, e.g. frictional interlocking, with a membrane and can be embodied as any kind of oscillatory fork or as a single rod. The membrane and the oscillatable element connected with the membrane, thus the oscillatable unit, are/is excited via a transmitting/receiving unit to execute oscillations. The transmitting/receiving unit is usually at least one piezoelectric, respectively electromechanical, element. Moreover, also so-called membrane oscillators are known, in the case of which the oscillatable element is composed only of a membrane.

Usually, a vibronic sensor is excited via an analog electronics to execute oscillations, wherein the analog electronics together with the oscillatable unit form the analog oscillatory circuit. Corresponding vibronic sensors, respectively vibronic measuring devices, are manufactured and sold in various embodiments by the applicant under the marks, LIQUIPHANT and SOLIPHANT.

Vibronic sensors enable detection of a process-specific parameter, such as the limit-level of a liquid or a solid in a container. Usually, for detection of a predetermined fill level (limit level), the sensor is operated with the resonant frequency of the oscillatable unit. By detecting the frequency change at a set phase of usually 90°, it can be detected whether the oscillatable unit is in contact with the medium or whether it is oscillating freely.

Moreover, it is known to determine, respectively to monitor, other process specific parameters in a medium by evaluating the oscillatory behavior of vibronic sensors. These process-specific parameters include especially the density and the viscosity, however, also the temperature, of the medium. For the purpose of determining the density of a liquid medium, the phase difference (often also referred to simply as phase) between the input signal and the output signal is set to 45° or −135°. In setting this phase difference, a frequency change is unequivocally attributable to a change of the density of the medium, since an influencing by the viscosity of the fluid medium can be excluded. Published International Patent Application WO 02/031471 A2 describes an apparatus for viscosity measurement. Known from European Patent EP 2 041 529 B1 is an apparatus for determining the density of a liquid medium.

As evident based on the above mentioned examples, an analog electronics has the disadvantage that it is relatively inflexible. Especially, the analog electronics must be matched to each sensor, respectively sensor type, as a function of its oscillation characteristics and further as a function of the respective application—thus whether the sensor is to be applied for fill level-, density- or viscosity measurement. A solution, which avoids the above mentioned disadvantages, is described in applicant's German Application DE 10 2012 113 045.0, filed on Dec. 12, 2012. The content of DE 10 2012 113 045.0 is incorporated here by reference.

The portfolio of vibronic sensors is quite variant rich. Examples of this are the products of the applicant manufactured and sold under the marks, LIQUIPHANT and SOLIPHANT. Thus, it can be stated that known and future sensors do and will differ relatively strongly as concerns their geometry. In the case of the solution proposed in DE 10 2012 113 045.0, for the purpose of analytical determining the interaction between the oscillatable unit embodied as an oscillatory fork and the fluid medium, the two fork tines of the oscillatory fork are approximated via a mathematical model. In the concrete case, the two fork tines are approximated mathematically as ideal elliptical cylinders.

In order to transfer the method known from DE 10 2012 113 045.0 to oscillatable units with a different geometry, it is necessary to modify the mathematical model correspondingly. In such case, it is to be noted that the mathematical description of the interaction, respectively the interaction, between the oscillatable unit and the medium is relatively complex. Added to this are two other considerations:

due to the complex geometry of the oscillatable unit, there are always small discrepancies between the modeled and the real situation; and the geometries of the oscillatable units of a sensor type, e.g. LIQUIPHANT T or LIQUIPHANT M, are usually, e.g. due to manufacturing tolerances, never one hundred percent in agreement.

Both aspects act unfavorably on the desired high accuracy of measurement of vibronic sensors.

SUMMARY OF THE INVENTION

An object of the invention is to provide a method, with which the accuracy of measurement of a vibronic sensor, respectively vibronic measuring device, can be improved.

The object is achieved by a method for calibration or adjustment of any oscillatable unit with a mathematical model describing the oscillatable unit, wherein the oscillatable unit interacts at least at times with a medium located in a container and is utilized for ascertaining or monitoring at least one process- and/or system specific parameter in automation technology, wherein the oscillatable unit is excited via a real input signal to execute oscillations; wherein the real output signal of the oscillatable unit is ascertained; wherein the real output signal is digitized and a real output sequence produced; wherein the real input signal is digitized and a digital input sequence produced; wherein the digital input sequence is fed to a function block, which provides the mathematical model of the oscillatable unit in interaction with the medium, wherein the mathematical model is defined by at least two sensor-specific variables; wherein a virtual output sequence is produced via the mathematical model; wherein the virtual output sequence is compared with the real output sequence; wherein in the case of a deviation, the sensor-specific variables of the mathematical model are adaptively changed until the deviation between the virtual output sequence and the real output sequence of the oscillatable unit lies within a predetermined tolerance range.

The differential equation of a vibronic sensor is—such as derived in DE 10 2012 113 045.0—an equation of second order:

$$U_e * \omega_0^2 = \ddot{\phi} + 2*D*\omega_0*\dot{\phi} + \omega_0^2*\phi$$

For the eigen angular frequency $\omega_0$ and Lehr's damping mass D, the following formulas result:

$$\omega_0^2 = \frac{c(T)}{m_s + m_F}$$

$$D = \frac{d_S + d_F}{2*(m_S + m_F)*\omega_0}$$

The total force $F_F$ exerted by the fluid medium on the body results from summing the pressure force $F_D$ and the frictional force $F_R$. In such case, the direction of the individual forces is to be taken positive in each case:

$$F_F = F_D + F_R$$

$$F_F = m_F \cdot \frac{du}{dt} + d_F \cdot u$$

$m_F$ is interpreted as supplementally on-coupling mass and $d_F$ as supplementally acting damping:

$$m_F = G_1 \cdot \rho + G_2 \cdot \sqrt{\frac{\rho \eta}{2\omega}}$$

$$d_F = G_2 \cdot \sqrt{\frac{\omega \rho \eta}{2}}$$

G1, G2 are parameters, which depend exclusively on the geometry of the oscillatable body.

For the case, in which the oscillatable system is approximated by two elliptical fork tines, the following equations hold:

$$m_F = 2 \cdot l \cdot b \cdot X \cdot \sqrt{\frac{2\rho\eta}{\omega}} + l \cdot \rho \cdot a^2 \cdot \pi$$

$$d_F = 2 \cdot l \cdot b \cdot X \cdot \sqrt{2\omega\rho\eta}$$

The stiffness of the oscillatable unit is given by c(T), $m_S$ is the mass, $d_S$ the damping of the freely oscillating oscillatable unit, D Lehr's damping mass and $\omega_0$ the eigenfrequency. The sensor-specific variables, especially the geometric parameters, can be determined via a parameter estimation method.

Information for defining the eigenfrequency and the resonant frequency will now be given:

The resonant frequency $\omega_r$ is always the frequency, at which the maximum amplitude occurs.

The eigenfrequency $\omega_d$ is the frequency, with which an oscillatable unit oscillates freely.

In the undamped case, a phase of 90° occurs between transmitting- and received signals, when the oscillatable unit is excited with the eigenfrequency. In this special case, the eigenfrequency is referenced with $\omega_0$.

The eigen- and resonant frequencies differ from one another additionally in the damped case.

In the case of vibronic sensors, the exciting occurs always with the eigenfrequency of the undamped oscillating oscillatable unit, in the case of which a phase of 90° occurs. The eigenfrequency can be ascertained with following formula:

$$\omega_0 = \sqrt{\frac{c}{m}}$$

In the undamped as well as also in the damped case, $\omega_0$ can be calculated with the above formula. In these cases, one obtains the frequency, in the case of which a phase of 90° results. In the damped case, corresponds, however, neither to the resonant frequency $\omega_r$, nor to the eigenfrequency $\omega_d$ of the damped system. These are defined as follows, wherein c is the stiffness, m the mass, $\omega_0$ the undamped eigenfrequency, $\omega_d$ the damped eigenfrequency, $\omega_r$ the resonant frequency and D Lehr's damping mass.

$$\omega_d = \omega_0 \sqrt{1-D^2}$$

$$\omega_r = \omega_0 \sqrt{1-2D^2}$$

After termination of the preferably automatically running calibration method of the invention, the process-specific parameters, especially the fluid parameters, density $\rho$, viscosity $\eta$ and temperature T, can be ascertained via a parameter estimation method in a subsequent adjustment method. While in the case of performing the method described in DE 10 2012 113 045.0 for determining and/or monitoring process parameters the sensor-specific parameters $G_1$, $G_2$ are held constant, in the case of the solution of the invention especially the above-mentioned process-specific parameters are held constant. Then, according to the invention, the sensor-specific parameters are varied until the deviation between the virtual output sequence and the real output sequence of the oscillatable unit lies within a predetermined tolerance range or preferably goes to zero. For this, the oscillatable unit, respectively the vibronic sensor, must be operated in a defined medium at a constant temperature.

The method of the invention is preferably placed in front of the method described in DE 10 2012 113 045.0. The adjustment per model provided by the invention enables matching at least two sensor-specific variables, which decisively influence the interaction between the oscillatable unit and the medium, adaptively to the real behavior of the oscillatable unit. The terminology, sensor-specific variables, means here, besides the already multiply mentioned geometric parameters, also variables, which determine the interacting behavior of the sensor with the medium, such as the material properties of the oscillatable unit or mass ratios of the oscillatable unit.

The method of the invention has the decisive advantage that an existing model, e.g. the model described in DE 10 2012 113 045.0 in detail for two elliptical fork tines, can be matched to any, and the most varied of, sensor-specific variables, respectively geometric parameters, without requiring for this the investing of effort into the rewriting of the mathematical model. While in DE 10 2012 113 045.0 e.g. the geometric parameters are held constant, the geometric parameters or other sensor-specific variables in the case of the solution of the invention are adaptively changed until the model behavior and the behavior of the real oscillatable unit highly accurately agree. This adaptive approximation process runs automatically. According to the invention, it is possible for the first time—independently of the actual embodiment of the oscillatable unit—, always to achieve high agreement between any oscillatable unit and a corresponding mathematical model.

As already indicated earlier, the oscillatable unit is associated with a sensor or measuring device of automation technology especially used to determine the fill level, respectively the limit-level, the density or the viscosity of a medium in a container.

An advantageous further development of the method of the invention provides that the oscillatable unit is operated at an eigenfrequency. However, it is completely sufficient when the oscillation frequency of the oscillatable unit lies in the vicinity of the resonant frequency of the mechanical oscillatory system. This need not be identical with the eigenfrequency.

In a preferred embodiment of the solution of the invention, the adjustment, respectively the calibration, of the oscillatable unit in the medium occurs under defined process-, respectively system specific, conditions. Especially, the temperature of the calibration medium is held constant. The same holds for the viscosity and the density of the calibration medium. Additionally, attention must be paid that the medium-contacting part of the oscillatable unit during the adjustment is always in contact with the medium to a defined immersion depth.

Furthermore, it is provided that the sensor-specific variables, especially the geometric parameters, ascertained during the adjustment or the calibration are transmitted into a memory of the sensor, respectively of the measuring device. As already mentioned above, the ascertained sensor-specific variables, respectively the geometric parameters, of the earlier adjusted, respectively calibrated, oscillatable unit are subsequently utilized in the regular measurement operation of the measuring device, respectively of the sensor, for ascertaining the process- and/or system specific parameters. A preferred method for doing this is described in detail in the above cited DE 10 2012 113 045.0.

Both for ascertaining the sensor-specific variables, respectively the geometric parameters, as well as also for ascertaining the process- and/or system specific parameters, a description of the oscillatable unit in a state space or as a transfer function is used as mathematical model, which describes the oscillatable unit as a linear or nonlinear system. Especially, the mathematical model, in which the oscillatable unit is described as a linear or nonlinear system, is expanded by the variables to be determined, in order to use a parameter estimation method. The applicable mathematical model describes, by transfer functions or transfer matrices, the relationship between the input signal and the output signal. Parameter estimation methods for mathematical models in the form of a transfer function include: the method of least squares, the generalized LS method, the RLS method, the method of auxiliary variables and the method of maximum probability. Preferably used as parameter estimation method for mathematical models in the state space is the extended Kalman filter, the unscented Kalman filter or a subspace method.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
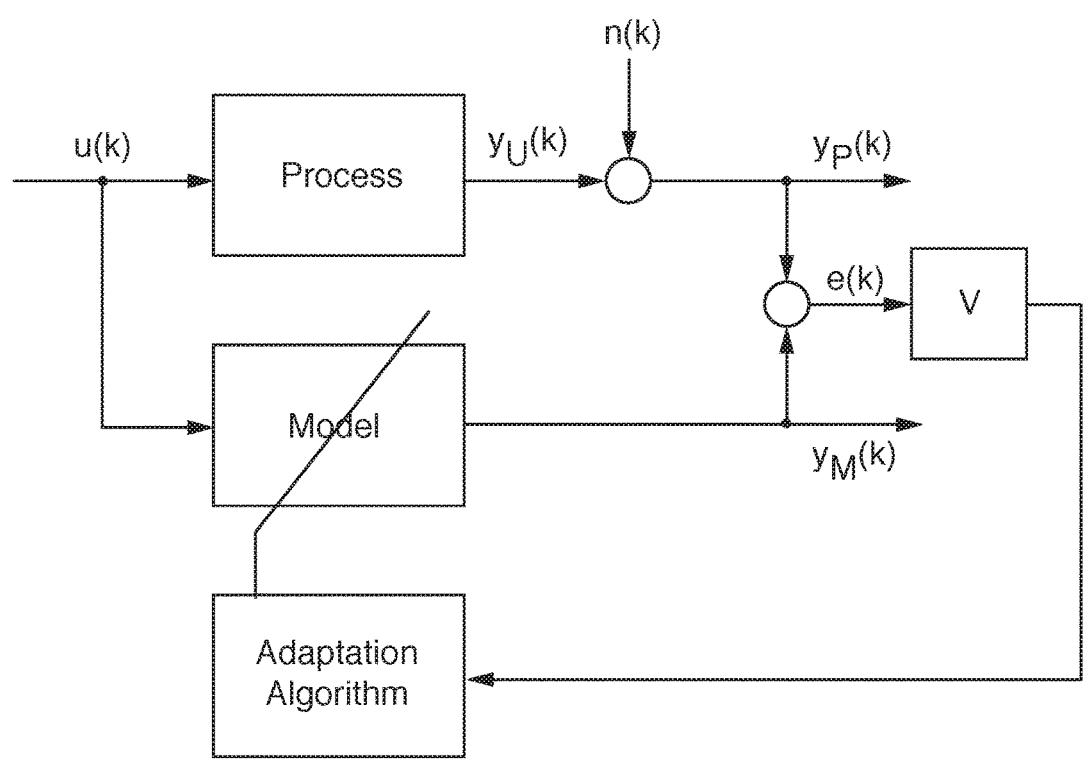
FIG. 1 is a block diagram illustrating the method of the invention.

FIG. 1 shows a block diagram illustrating the method of the invention for determining and or monitoring at least one sensor-specific variable, especially two geometric parameters. For performing the method of the invention, the oscillatable unit is at least at times in contact with a medium, respectively fluid, located in a container. The oscillatable unit in contact with the medium, respectively fluid, is referenced in FIG. 1 using the label "Process".

The oscillatable unit is excited via an analog input signal to execute oscillations. The real output signal is ascertained as output signal of the oscillatable unit and then digitized, so that a real output sequence yu(k) is produced. In the illustrated case, also a disturbing variable n(k) is utilized, so that the real output sequence yp(k) results.

In parallel with this, the real input signal is digitized; so that a digital input sequence u(k) is produced. The digital input sequence u(k) is fed to a function block—here labeled Model—, which provides at least one mathematical model of the oscillatable system in interaction with the medium. The mathematical model is defined by a number of process- and/or system specific parameters. The mathematical model produces a virtual output sequence ym(k). Then, the virtual output sequence ym(k) is compared with the real output sequence yu(k), respectively yp(k). In the case of a deviation e(k), at least one of the process- or system specific parameters—in the case of the method of DE 10 2012 113 045.0—or the sensor-specific variables—in the case of the method of the invention—of the mathematical model is adaptively changed, until the deviation e(k) between the virtual output signal ym(k) and the real output signal yu(k), respectively yp(k), of the oscillatable unit lies within a predetermined tolerance range. Then, the adaptively ascertained parameters G1, G2; η, ρ, T are provided.

Figure 2:
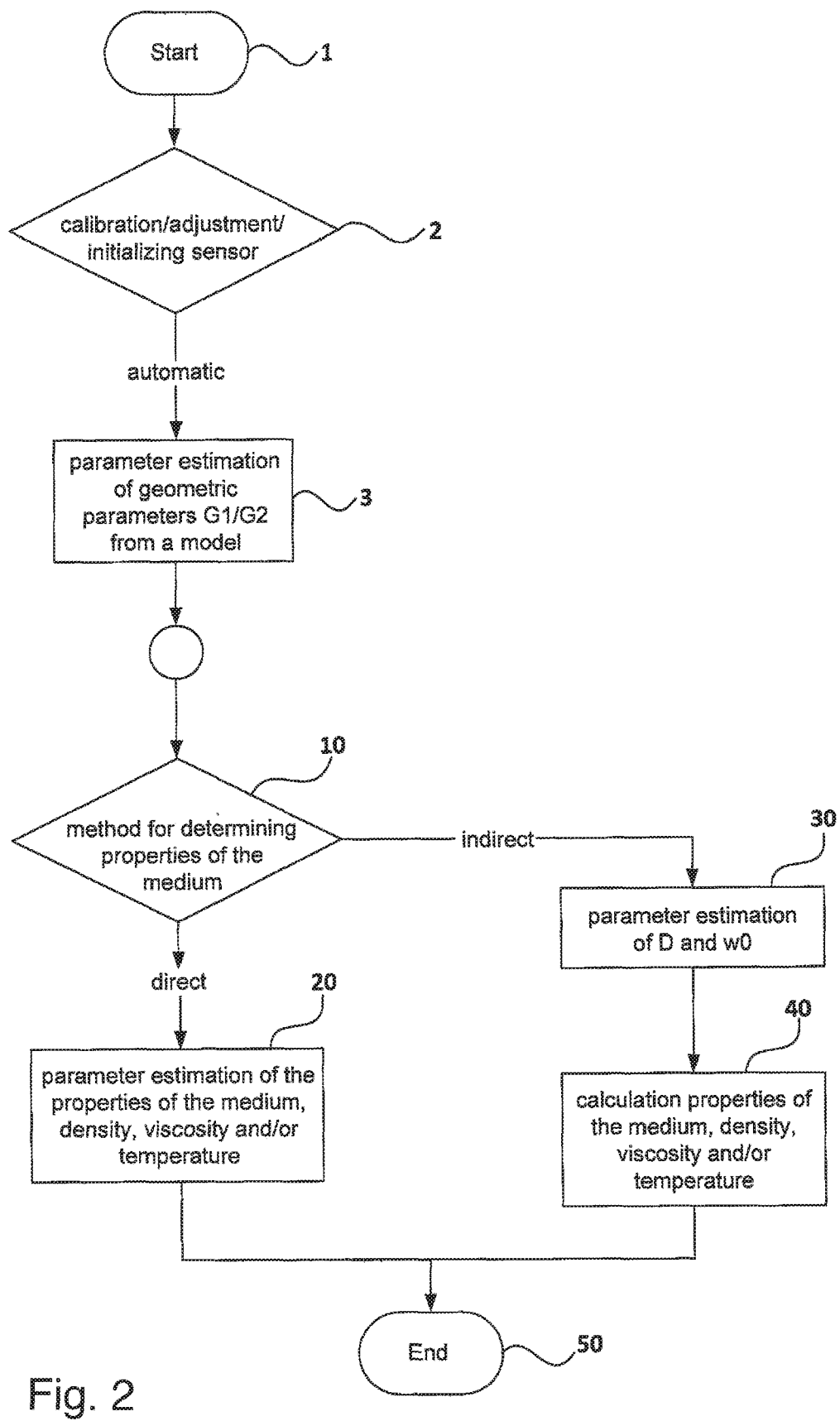
FIG. 2 is a flow diagram, which shows the method steps of the method of the invention and the method proposed in DE 10 2012 113 045.0.
Figure 2A:
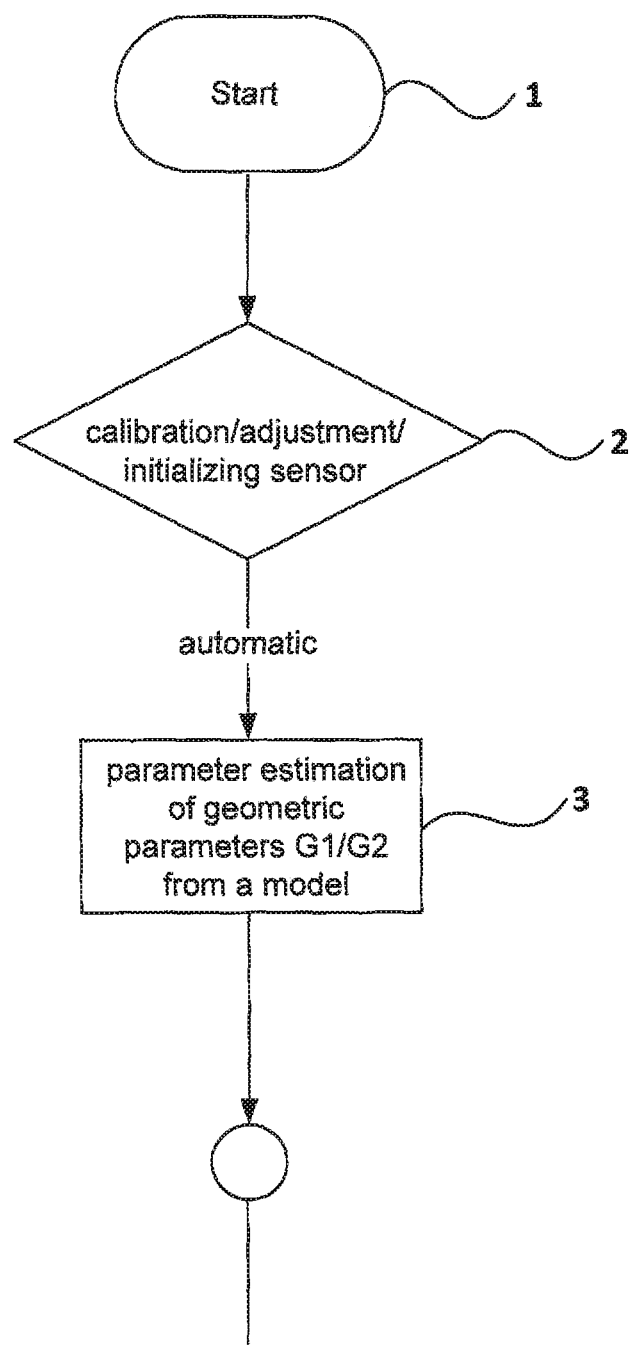
FIG. 2a is an enlargement of the individual method steps of the method of the invention shown in FIG. 2.

FIG. 2 shows a flow diagram, which illustrates the program steps 1-3 of the method of the invention—see also the enlargement in FIG. 2a—and the program steps 10, 20, 30, 40, 50 of the method described in DE 10 2012 113 045.0.

The method of the invention for calibration or adjustment of any oscillatable unit using a mathematical model describing the oscillatable unit is started at the program point 1. At program point 2, the calibrating, respectively the adjustment, starts, the sensor is initialized. Then, at program point 3, the sensor-specific variables, here the geometric parameters G1, G2, are automatically ascertained via e.g. one of the above mentioned parameter estimation methods.

After the start of the method, it is decided at program point 10, whether the properties of the medium, respectively the process-specific parameters ρ, η, T, are to be ascertained directly or indirectly via the parameter estimation method. If the direct path is selected, then the parameter estimating of the process-specific parameters ρ, η, T occurs at program point 20.

If the indirect path is selected, then, at the program point 30, a parameter estimating of Lehr's damping mass D and the eigen angular frequency $\omega_0$ is performed. Then, at the program point 40, the calculating of the properties of the medium, respectively the process-specific parameters $\rho$, $\eta$, T, is performed. The required process-specific parameters $\rho$, $\eta$, T are output at program point 50.

The invention claimed is:

1. A method for calibrating or adjustment of an oscillatable unit of a vibronic sensor with a mathematical model describing the oscillatable unit, the oscillatable unit interacts with a medium located in a container and is utilized for ascertaining or monitoring at least a limit level, a density, a viscosity or a temperature of said medium in automation technology, comprising the steps of:

exciting the oscillatable unit via a real input signal to execute oscillations;
    ascertaining the real output signal of the oscillatable unit;
    digitizing the real output signal and producing a real output sequence;
    digitizing the real input signal and producing a digital input sequence;
    feeding said digital input sequence to a function block, which provides the mathematical model of the oscillatable unit in interaction with the medium, said mathematical model being defined by at least two sensor-specific variables, wherein said sensor-specific variables are geometric parameters, material properties or mass ratios of the oscillatable unit;
    producing a virtual output sequence via said mathematical model; and
    comparing the virtual output sequence with the real output sequence;
    wherein in the case of a deviation, the sensor-specific variables of said mathematical model are adaptively changed, until the deviation between the virtual output sequence and the real output sequence of the oscillatable unit lies within a predetermined tolerance range, and
    wherein the oscillatable unit is associated with a sensor or a measuring device, which is used to determine fill level, density ($\rho$) or viscosity ($\eta$) of the medium in the container, and
    wherein the sensor-specific variables or the geometric parameters (G1, G2) ascertained during the adjustment or the calibration are transmitted into a memory of the sensor, respectively of the measuring device.

2. The method as claimed in claim 1, wherein:
the oscillatable unit is operated at an eigenfrequency.

3. The method as claimed in claim 1, wherein:
the adjustment, respectively the calibration, of the oscillatable unit is performed in the medium under defined process-, respectively system specific, conditions.

4. The method as claimed in claim 3, wherein:
during the adjustment or the calibration, the viscosity ($\eta$) and the density ($\rho$) of the medium are held constant and wherein the medium-contacting part of the oscillatable unit is in contact with the medium to a defined immersion depth.

5. The method as claimed in claim 1, wherein:
the sensor-specific variables of the earlier adjusted, respectively calibrated, oscillatable unit are utilized in measurement operation of the sensor, respectively of the measuring device, for ascertaining process- and/or system specific parameters ($\rho$, $\eta$, T).

6. The method as claimed in claim 1, wherein:
for ascertaining the sensor-specific variables, respectively the geometric parameters, and for ascertaining the process- and/or system specific parameters ($\rho$, $\eta$, T), a description of the oscillatable unit in a state space or as transfer function is used as mathematical model, which describes the oscillatable unit as a linear or nonlinear system.

7. The method as claimed in claim 6, wherein:
used as adaptation algorithm in the mathematical model for determining unknown parameters is a parameter estimation method, in which the oscillatable unit is described as a linear or nonlinear system and which describes the relationship between the input signal and the output signal by transfer functions or transfer matrices.

8. The method as claimed in claim 7, wherein:
used as parameter estimation method for mathematical models in the form a transfer function is preferably the method of least squares, the generalized LS method, the RLS method, the method of auxiliary variables or the method of maximum probability.

9. The method as claimed in claim 6, wherein:
used as parameter estimation method for mathematical models in state space is preferably the extended Kalman filter, the unscented Kalman filter or a subspace method.

* * * * *